(12) United States Patent
Swain et al.

(10) Patent No.: US 10,859,527 B2
(45) Date of Patent: Dec. 8, 2020

(54) ELECTRODE AND SENSOR APPARATUS AND RELATED METHODS FOR DETECTION OF NITRIC OXIDE AND PEROXYNITRATE

(71) Applicant: BOARD OF TRUSTEES OF MICHIGAN STATE UNIVERSITY, East Lansing, MI (US)

(72) Inventors: Greg M. Swain, Owosso, MI (US); Serban F. Peteu, East Lansing, MI (US); Borys W. Hrinczenko, East Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 394 days.

(21) Appl. No.: 15/885,024

(22) Filed: Jan. 31, 2018

(65) Prior Publication Data

US 2018/0217087 A1  Aug. 2, 2018

Related U.S. Application Data

(60) Provisional application No. 62/453,203, filed on Feb. 1, 2017.

(51) Int. Cl.
*A61B 5/097* (2006.01)
*G01N 27/407* (2006.01)
(Continued)

(52) U.S. Cl.
CPC ......... *G01N 27/4075* (2013.01); *A61B 5/082* (2013.01); *A61B 5/097* (2013.01);
(Continued)

(58) Field of Classification Search
CPC .............................. A61B 5/082; A61B 5/097
See application file for complete search history.

(56) References Cited

U.S. PATENT DOCUMENTS 6,592,519 B1 * 7/2003 Martinez ................ A61B 5/145
600/309

OTHER PUBLICATIONS

Peteu et al., "Electrochemical detection of peroxynitrite using hemin-PEDOT functionalize boron-doped diamond," Analyst, vol. 141, pp. 1796-1806 (available online Feb. 2, 2016).

* cited by examiner

*Primary Examiner* — Puya Agahi
(74) *Attorney, Agent, or Firm* — Marshall, Gerstein & Borun LLP

(57) ABSTRACT

The disclosure relates to electrodes and related sensor apparatus for the detection of nitric oxide (NO) and/or peroxynitrite (PON). The electrodes and sensors incorporate electrically conducting boron-doped diamond (BDD) to provide a selective and quantitative detection platform. The sensing electrode for detection of NO includes metallic nanoparticles for oxidation of NO as well as anionic polyelectrolyte layer over the electrically conducting BDD layer. The sensing electrode for detection of PON includes an electrically conductive polymeric layer including a metal-complexed porphyrin for redox reaction with PON over the electrically conducting BDD layer. A corresponding sensor apparatus includes one or two electrochemical cells with associated electrolytes, separate working electrodes for the separate, selective detection of NO or PON, and associated reference electrode(s) and counter electrode(s). Use of the related sensor with various electrochemical techniques to detect NO and/or PON in exhaled breath can be used for detection and/or diagnosis of lung-related conditions.

11 Claims, 6 Drawing Sheets

(51) Int. Cl.
*G01N 27/404* (2006.01)
*G01N 27/413* (2006.01)
*A61B 5/08* (2006.01)

(52) U.S. Cl.
CPC ..... *G01N 27/4045* (2013.01); *G01N 27/4072* (2013.01); *G01N 27/4074* (2013.01); *G01N 27/4076* (2013.01); *G01N 27/413* (2013.01); *A61B 2562/028* (2013.01); *A61B 2562/125* (2013.01)

ELECTRODE AND SENSOR APPARATUS AND RELATED METHODS FOR DETECTION OF NITRIC OXIDE AND PEROXYNITRATE

CROSS REFERENCE TO RELATED APPLICATION

Priority is claimed to U.S. Provisional Application No. 62/453,203 filed Feb. 1, 2017, which is incorporated herein by reference in its entirety.

STATEMENT OF GOVERNMENT INTEREST

This invention was made with government support under DK094932 awarded by the National Institutes of Health. The government has certain rights in the invention.

BACKGROUND OF THE DISCLOSURE

The disclosure relates to electrodes and related electrochemical sensor apparatus for the detection of nitric oxide (NO) and peroxynitrite (PON). The electrodes and sensors incorporate electrically conducting boron-doped diamond to provide a stable and reproducible detection platform. The disclosure further relates to the use of the sensors to detect NO and PON in exhaled breath, such as using a prototype analyzer cell as illustrated in the examples. Such an analyzer could be used for detection and/or diagnosis of respiratory diseases, for example lung-related conditions or otherwise.

SUMMARY

In one embodiment, the disclosure relates to a sensing electrode for detection of nitric oxide (NO), the electrode comprising: (a) an electrically conducting substrate; (b) an electrically conducting boron-doped diamond (BDD) layer over the electrically conducting substrate (e.g., a semi-metallic diamond film; thin polycrystalline film suitably 1-5 μm thick, for example having a thickness of at least 0.2, 1, 2, or 3 μm and/or up to 3, 5, 8 or 10 μm; can be directly deposited by chemical vapor deposition on the electrically conducting substrate; the BDD is preferably polycrystalline diamond, for example having a nanocrystalline morphology grown with hydrogen-rich source gas mixtures or an ultrananocrystalline morphology grown with argon-rich source gas mixtures); (c) metallic nanoparticles for oxidation of nitric oxide (NO), the metallic nanoparticles being deposited on the electrically conducting BDD layer (e.g., at least 0.5, 1, 2, 3, 5, or 10 nm and/or up to 5, 10, 20, 50, or 100 nm diameter for nanoparticles, which can be an average diameter, such as a number-, weight-, or volume-average diameter; metallic nanoparticles can serve to catalyze the oxidation of NO, for example to nitrous acid ($HNO_2$) and/or other oxidation products); and (d) an anionic polyelectrolyte layer over the metallic nanoparticles and the electrically conducting BDD layer (e.g., can be formed as a film or microporous membrane covering and in contact with the diamond semiconductor layer and the catalytic metallic nanoparticles thereon; anionic polyelectrolyte layer is impermeable to anions generally, in particular $NO_2^-$ and peroxynitrite (PON) that could be in a breath sample being analyzed; anionic polyelectrolyte layer is permeable to NO (e.g., non-ionic species); the anionic polyelectrolyte layer is suitably 1-3 μm thick, for example having a thickness of at least 0.1, 1, or 2 μm and/or up to 2, 3, 5 or 10 μM).

Various refinements and embodiments of the sensing electrode for detection of nitric oxide (NO) are possible.

In a refinement, the electrically conducting substrate comprises platinum (e.g., in any desired shape, such as in the form of a wire or plate (at least 10, 20, or 50 μm and/or up to 50, 100, or 200 μm in diameter or thickness)). More generally, the electrically conducting substrate can be any desired electrically conductive material, metallic or otherwise, for example including other electrically conducting metals and boron-doped silicon.

In another refinement, the boron-doped diamond of the electrically conducting BDD layer has a carbon:boron (C:B) atomic ratio ranging from 100:1 to 100000:1 (e.g., with a carbon:boron (C:B) atomic ratio of at least 100:1, 200:1, 500:1, or 1000:1 and/or up to 1000:1, 2000:1, 5000:1, 10000:1, or 100000:1).

In another refinement, the metallic nanoparticles comprise platinum. In other refinements, the metallic nanoparticles more generally can comprise a metal selected from the group consisting of antimony, arsenic, bismuth, cadmium, chromium, cobalt, copper, germanium, gold, manganese, molybdenum, indium, iridium, lead, nickel, osmium, palladium, platinum, rhodium, ruthenium, silver, tin, zinc, and combinations thereof (e.g., metallic alloys thereof). In a particular refinement, the metallic nanoparticles can be essentially entirely comprised of platinum or a metallic alloy of platinum and one or more metallic elements such as those above.

In another refinement, the anionic polyelectrolyte comprises an anionic group selected from the group consisting of a sulfonic acid group, a carboxylic acid group, a derivative thereof, and combinations thereof (e.g., derivatives can include metallic or other salts of the acid group, deprotonated anions of the acid group, etc.; examples include a sulfonated tetrafluoroethylene copolymer (e.g., NAFION as below), polystyrene sulfonate (PSS), polyacrylic acid (PAA), etc.).

In another refinement, the anionic polyelectrolyte comprises a tetrafluoroethylene copolymer comprising tetrafluoroethylene monomer backbone units and pendant perfluorovinyl ether side chains with one or more sulfonic acid groups (e.g., a side chain terminated with a sulfonic acid group or derivative thereof; can be a NAFION membrane material available from DuPont).

In another embodiment, the disclosure relates to a sensing electrode for detection of peroxynitrite (PON), the electrode comprising: (a) an electrically conducting substrate; (b) an electrically conducting boron-doped diamond (BDD) layer over the electrically conducting substrate (e.g., a semi-metallic diamond film; thin polycrystalline film suitably 1-5 μm thick, for example having a thickness of at least 0.2, 1, 2, or 3 μm and/or up to 3, 5, 8 or 10 μm; can be directly deposited by chemical vapor deposition on the electrically conducting substrate; the BDD is preferably polycrystalline diamond, for example having a nanocrystalline morphology grown with hydrogen-rich source gas mixtures or an ultrananocrystalline morphology grown with argon-rich source gas mixtures); (c) an electrically conductive polymeric layer over the electrically conducting BDD layer (e.g., as a film or microporous membrane directly on the diamond layer; located on an exposed region such as on a distal or other tip portion of the electrode to be contacted with an electrolyte medium during detection; other portions of electrode can be covered/shielded with a housing such as a polypropylene or other non-conductive polymeric material), the electrically conductive polymeric layer comprising (i) an electrically conductive polymer and (ii) a porphyrin comprising a complexed metal ion (e.g., as composite film or membrane structure with the conductive polymer as the continuous matrix and the porphyrin distributed throughout the matrix; the polymeric layer is suitably 1-3 μm thick, for example having a thickness of at least 0.1, 1, or 2 μm and/or up to 2, 3, 5 or 10 μm); and (d) optionally a cationic polyelectrolyte layer over the electrically conductive polymeric layer (e.g., as a film or microporous membrane covering and in contact with the electrically conductive polymeric layer; cationic polyelectrolyte layer is impermeable to cations; cationic polyelectrolyte layer is permeable to PON (e.g., anionic or non-ionic species); the cationic polyelectrolyte layer is suitably 1-3 μm thick, for example having a thickness of at least 0.1, 1, or 2 μm and/or up to 2, 3, 5 or 10 μm).

Various refinements and embodiments of the sensing electrode for detection of peroxynitrite (PON) are possible.

In a refinement, the electrically conducting substrate comprises platinum (e.g., in any desired shape, such as in the form of a wire or plate (at least 10, 20, or 50 μm and/or up to 50, 100, or 200 μm in diameter or thickness)). The electrically conducting substrate more generally can be any desired electrically conductive material, metallic or otherwise, for example including other electrically conducting metals and boron-doped silicon.

In another refinement, the boron-doped diamond of the electrically conducting BDD layer has a carbon:boron (C:B) atomic ratio ranging from 100:1 to 100000:1 (e.g., with a carbon:boron (C:B) atomic ratio of at least 100:1, 200:1, 500:1, or 1000:1 and/or up to 1000:1, 2000:1, 5000:1, 10000:1, or 100000:1).

In another refinement, the electrically conductive polymer is selected from the group consisting of polyacetylenes, polyphenylene vinylenes, polypyrroles, polythiophenes; polyanilines, polyphenylene sulfides, derivatives thereof, and combinations thereof (e.g., derivatives can include substituted analogs of the various listed polymers with an electrically conducting backbone, such as poly(ethylenedioxythiophene) as a substituted polythiophene; combinations can include mixtures/blends of the various conductive polymers or copolymers of their monomers). In a particular refinement, the electrically conductive polymer comprises poly(ethylenedioxythiophene).

In another refinement, the porphyrin comprises hemin (i.e., protoporphyrin IX with a complexed ferric ion ($Fe^{3+}$) and chloride counter ion ligand). More generally, the porphyrin can include a substituted porphin core structure (e.g., a substituted porphyrin), a complexed metal ion (e.g., an ion in a +2 or a +3 oxidation state that is capable of further oxidation to a +3 or a +4 oxidation state during detection of PON), and a corresponding counter anion (e.g., chloride or other halogen anion). The substituted porphin core can include 1, 2, or more pendant acid groups (or corresponding salt or anionic groups), among other substituents such as pendant alkyl groups, pendant alkenyl groups, and pendant or fused aryl groups. Examples of pendant groups acid include carboxylic acid or carboxylate groups, sulfonic acid or sulfonate groups, etc. The pendant groups can be attached to the primary cyclic structure of the porphin and/or one of the pyrrole subunits thereof, for example via an alkylene linking group having 1-10 or 1-4 carbon atoms (e.g., a —$C_2H_4$— ethylene linking group between a porphin core/pyrrole subunit and carboxylic acid group as in protoporphyrin IX). Other suitable metal ions include manganese (e.g., $Mn^{2+}$ which can further oxidize to $Mn^{3+}$) or cobalt (e.g., $Co^{2+}$ or $Co^{3+}$ which can further oxidize to $Co^{3+}$ or $Co^{4+}$, respectively). Another suitable porphyrin includes phthalocyanine (e.g., further including a complexed metal ion).

In another refinement, the electrically conductive polymer and porphyrin are present in the polymeric layer in a molar ratio ranging from 1:1 to 20:1 for electrically conductive polymer monomer units:porphyrin (e.g., at least 1:1, 2:1, 3:1 or 5:1 and/or up to 5:1, 10:1, 15:1 or 20:1).

In another refinement, the electrically conductive polymer and porphyrin are present in the polymeric layer in a weight ratio ranging from 0.2:1 to 100:1 for electrically conductive polymer:porphyrin (e.g., at least 0.2:1, 1:1, 2:1, 3:1 or 5:1 and/or up to 2:1, 5:1, 10:1, 20:1, 50:1, or 100:1).

In another refinement, the cationic polyelectrolyte layer is present and comprises polyethyleneimine. Other suitable cationic polyelectrolytes include poly(allylamine hydrochloride) (PAH) and poly(diallyldimethylammonium chloride) (polyDADMAC).

In another embodiment, the disclosure relates to an electrochemical sensor or analyzer for detecting nitric oxide (NO) and peroxynitrite (PON), for example in exhaled breath, the sensor or analyzer comprising: (a) a first electrochemical cell comprising (i) a first housing defining a first internal cell volume, (ii) a first working electrode (WE1) in the first internal cell volume for detection of nitric oxide (NO) according to any of its variously disclosed refinements (e.g., a sensing electrode for detection of NO as described above), (iii) a first reference electrode (RE1) in the first internal cell volume, and (iv) optionally a first counter electrode (CE1) in the first internal cell volume; and (b) a second electrochemical cell comprising (i) a second housing defining a second internal cell volume, (ii) a second working electrode (WE2) in the second internal cell volume for detection of peroxynitrite (PON) according to any of its variously disclosed refinements (e.g., a sensing electrode for detection of PON as described above), (iii) a second reference electrode (RE2) in the second internal cell volume, and (iv) optionally a second counter electrode (CE2) in the second internal cell volume. The first and second electrochemical cells each can be configured to operate in a 2-electrode sensor system (i.e., omitting the counter electrode) or a 3-electrode sensor system (i.e., including the counter electrode). The illustrated embodiment (FIG. 1 below) includes two separate electrochemical cells, each with its own set of electrodes for the detection of NO or PON. In another embodiment (not shown), the electrochemical sensor can include a single electrochemical cell with associated liquid electrolyte and electrodes, including a first working electrode (WE1) for detection of NO and a second working electrode (WE2) for detection of PON (e.g., while including a single reference electrode (RE1) and optionally a single counter electrode (CE1) that can be used in combination with the two working electrodes WE1 and WE2).

Various refinements and embodiments of the electrochemical sensor for detecting nitric oxide (NO) and peroxynitrite (PON) are possible.

In a refinement, the first electrochemical cell further comprises a first gas-permeable membrane at a boundary of the first internal cell volume (e.g., microporous membrane; permitting a gas inlet into the first internal cell volume while retaining a liquid electrolyte medium inside the cell volume; first membrane can be positioned at an otherwise open portion of the first cell housing, thereby serving as a selective gas inlet into the cell); and the second electrochemical cell further comprises a second gas-permeable membrane at a boundary of the second internal cell volume (e.g., microporous membrane; permitting a gas inlet into the second internal cell volume while retaining a liquid electrolyte medium inside the cell volume; second membrane can be positioned at an otherwise open portion of the second cell housing, thereby serving as a selective gas inlet into the cell).

In a further refinement, the electrochemical sensor further comprises a sample gas flow inlet coupled to and in fluid communication with the first gas-permeable membrane and the second gas-permeable membrane (e.g., gas flow inlet can be a sampling tube or other conduit to receive exhaled breath from a person or animal, optionally along with a flow splitter (such as a Y-splitter) to deliver at least a portion of the exhaled breath to/through each gas-permeable membrane and into the interior cell volume of each electrochemical cell). Such a refinement can further include a filter at the inlet to remove particulate matter present in exhaled animal or human breath. The filter could be disposable and used once, being discarded after receiving an exhaled breath sample from a user.

In another further refinement, the first gas-permeable membrane comprises an anionic polyelectrolyte membrane (e.g., a NAFION membrane or other anionic polyelectrolyte as above for the NO sensor); and the second gas-permeable membrane comprises a polysiloxane membrane. More generally, any suitable membrane can be used as long as they are permeable to NO (first membrane) and/or PON (second membrane). Each sensing electrode is selective for only one of the NO/PON analytes, so if the solution in the cell were to have both analytes present, the sensor would respond to only one.

In another refinement, the first reference electrode (RE1) and the second reference electrode (RE2) are Ag/AgCl electrodes; and the first counter electrode (CE1) and the second counter electrode (CE2) are platinum wire electrodes.

In another embodiment, the disclosure relates to a method for detecting nitric oxide (NO) and peroxynitrite (PON), the method comprising: (a) providing an electrochemical sensor for detecting nitric oxide (NO) and peroxynitrite (PON) according to any of its variously disclosed embodiments, wherein: the first electrochemical cell further comprises a first liquid electrolyte medium in the first internal cell volume with the WE1, RE1, and CE1 electrodes immersed therein, and the second electrochemical cell further comprises a second liquid electrolyte medium in the second internal cell volume with the WE2, RE2, and CE2 electrodes immersed therein; (b) delivering a sample containing or suspected of containing at least one of nitric oxide (NO) and peroxynitrite (PON) to the first liquid electrolyte medium and the second liquid electrolyte medium (e.g., different portions of the same sample are introduced into the first and second cells and the corresponding liquid electrolyte media); and (c) electrochemically detecting the nitric oxide in the first electrochemical cell, if present, and electrochemically detecting the peroxynitrite in the second electrochemical cell, if present.

Various refinements and embodiments of the method for detecting nitric oxide (NO) and peroxynitrite (PON) are possible.

In a refinement, the first liquid electrolyte medium and the second liquid electrolyte medium comprises a phosphate-buffered saline solution (e.g., more generally, any suitable electrolyte solutions could be used, and a phosphate-buffered saline solution around pH 7 is particularly suitable).

In another refinement, the sample contains at least one of nitric oxide and peroxynitrite as a target analyte.

In another refinement, electrochemical detection comprises: applying a first voltage differential to the first electrochemical cell WE1, RE1, and CE1 electrodes measuring a corresponding electrical current though the first electrochemical cell; and applying a second voltage differential to the second electrochemical cell WE2, RE2, and CE2 electrodes measuring a corresponding electrical current though the second electrochemical cell. For example, detection can include applying a fixed voltage differential and measuring a corresponding fixed current, applying a time-variable voltage differential and measuring a corresponding time-variable current such as in cyclic voltammetry. For instance, a bias potential is applied across the WE and RE, and the current is measured between the WE and CE. In addition to general voltammetry and amperometry, other suitable electrochemical methods for use with the sensor could include coulometry and/or electrochemical impedance spectroscopy. The same or different electrochemical methods can be applied to two different cells/sensors.

In another refinement, the method further comprises: (d) quantitatively determining the amount of the nitric oxide and the peroxynitrite in the sample (e.g., as a result of a calibration curve of concentration vs. measured current at known/fixed voltage differential). In a further refinement, the sample is an exhaled breath sample from a human or animal; and the method further comprises: (e) detecting in the human or animal one or more of lung transplant rejection, cancer, airway inflammation, cystic fibrosis, chronic obstructive pulmonary disease (COPD), asthma, and obliterative bronchitis based on one or more of the determined amount of nitric oxide and the determined amount of peroxynitrite. For example, detection of lung transplant rejection, cancer, airway inflammation, cystic fibrosis, chronic obstructive pulmonary disease (COPD), and/or asthma can be based on NO concentration; detection of obliterative bronchitis can be based on PON concentration. Detection can include a positive diagnosis based the electrochemical detection, or it can be an indication that further tests for a specific condition are to be performed. The quantitative detection/determination of NO and PON concentrations as well as the ratio of their concentrations can be useful in making diagnostic determinations. The ratio of PON to NO can be an important diagnostic for assessment of inflammation status. Specific concentrations of each PON and/or NO could also be useful for disease management. For example, NO levels below a certain concentration might correlate with good respiratory health while levels above this threshold might correlate with poor health condition. In asthma, for example, the threshold levels for NO are known.

In another refinement, the sample is an exhaled breath sample from a human or animal.

In another refinement, the electrochemical sensor comprises the first gas-permeable membrane and the second gas-permeable membrane of any of the foregoing embodiments; the electrochemical sensor comprises the sample gas flow inlet of any of the foregoing embodiments; and delivering the sample comprises exhaling the breath sample into the gas flow inlet such that any nitric oxide present in the breath sample passes through the first gas-permeable membrane and into the first liquid electrolyte medium of the first electrochemical cell, and any peroxynitrite present in the breath sample passes through the second gas-permeable membrane and into the second liquid electrolyte medium of the second electrochemical cell.

BRIEF DESCRIPTION OF THE DRAWINGS

For a more complete understanding of the disclosure, reference should be made to the following detailed description and accompanying drawings wherein:

FIG. 2 (B) illustrates a peroxynitrite sensor electrode according to the disclosure.

Figure 1:
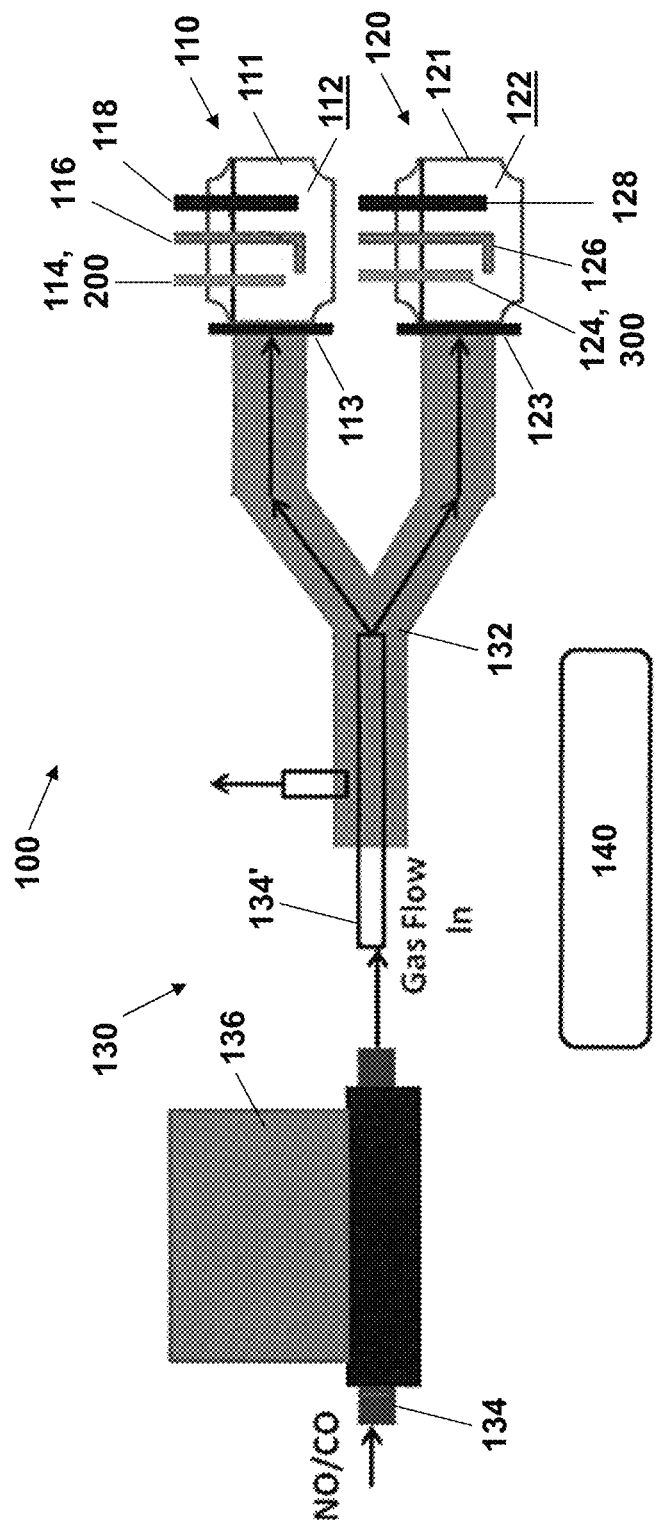
FIG. 1 illustrates an electrochemical sensor according to the disclosure for detection of nitric oxide and peroxynitrite.

While the disclosed apparatus, compounds, methods and compositions are susceptible of embodiments in various forms, specific embodiments of the disclosure are illustrated (and will hereafter be described) with the understanding that the disclosure is intended to be illustrative, and is not intended to limit the claims to the specific embodiments described and illustrated herein.

DETAILED DESCRIPTION

The disclosure relates to electrodes and related sensor apparatus for the detection of nitric oxide (NO) and/or peroxynitrite (PON). The electrodes and sensors incorporate electrically conducting boron-doped diamond (BDD) to provide a selective and quantitative detection platform. The sensing electrode for detection of NO includes metallic nanoparticles for oxidation of NO as well as anionic polyelectrolyte layer over the electrically conducting BDD layer. The sensing electrode for detection of PON includes and electrically conductive polymeric layer including a metal-complexed porphyrin for redox reaction with PON over the electrically conducting BDD layer. A corresponding sensor apparatus includes one or two electrochemical cells with associated electrolytes, separate working electrodes for the separate, selective detection of NO or PON, and associated reference electrode(s) and counter electrode(s). Use of the related sensor with various electrochemical techniques to detect NO and/or PON in exhaled breath can be used for detection and/or diagnosis of lung-related conditions.

Lung transplantation is a therapeutic option for patients suffering from the end stage of various lung diseases. Diseases such as chronic obstructive pulmonary disease (COPD), pulmonary fibrosis, and cystic fibrosis can damage lungs beyond repair of medication. In these cases, a lung transplant is necessary for the survival of the patient. Since 1988, over 33,000 lung transplants have been performed. After transplantation, the risk of rejection or infection is high with only 45% of patients surviving to year 5.

Lung transplant rejection is common with around 60% of lung transplant patients experiencing an episode of acute rejection within their first year. The current method of detection is to take a small portion of the lung and biopsy to look for rejection. This is an invasive process that if done infrequently can lead rejection progressing extensively before detection. A non-invasive method of monitoring rejection in lung transplant patients is exhaled nitric oxide (NO) levels. NO is an exhaled gas that is a marker of airway inflammation and has been used to detect asthma. NO levels are significantly higher in patients suffering from acute lung rejection than in healthy patients. Measuring the output of NO in exhaled breath could be used as indicator for acute lung rejection. NO levels, however, do not indicate the presence of an infection such as obliterative bronchiolitis (OB).

OB is inflammation that leads to the progressive narrowing of airways. If bronchiolitis obliterans syndrome (BOS), develops, a decline in pulmonary function leads to patient death typically within 5 years on onset. This is often referred to as chronic rejection. BOS is the leading cause of patient mortality after 1 year post transplant. The presence of OB is often missed in lung biopsies, leading to undetected progression of the inflammation. In the late 1990's peroxynitrite, a potent oxidizing agent, was discovered to be a marker for OB in tissue samples. Increased levels of peroxynitrite, is also founds in the sputum of patients suffering from chronic obstructive pulmonary disease (COPD).

This disclosure describes a sensor to provide detection of low levels (parts per billion) nitric oxide and peroxynitrite (e.g., at concentrations of at least 1, 2, 5, or 10 ppb and/or up to 10, 20, 50, 100, 200, or 500 ppb, such in an original exhaled breath gaseous sample). An illustrative design is shown in FIG. 1 for a breath analyzer/electrochemical sensor 100 to detect nitric oxide and peroxynitrite. The patient breathes into a disposable particulate filter 134 inlet that is a component of a sample gas flow inlet 130 and is connected to the analyzer 100 via a mass flow controller 136 and a fluid communication conduit 132 (e.g., a flow splitter as illustrated). The mass flow controller 136 then regulates the gas flow and composition incident on two electrochemical sensors 200, 300 via the fluid communication conduit 132. In some embodiments, the patient can breathe into the fluid communication conduit 132, and the mass flow controller 136 can be omitted. For example the patient can breathe into a disposable particulate filter 134' inlet attached to the conduit 132 and positioned at the location where the mass flow controller 136 outlet is illustrated. The two electrochemical sensors 200, 300 are utilized for the detection of nitric oxide and peroxynitrite, respectively. The gas flow is applied to gas permeable membranes 113, 123 that separate the thin solution layers housing the two sensors 200, 300 in housings 111, 121 defining corresponding internal cell volumes 112, 122. The external flow causes an equilibrium concentration of the gas to be established in the solution phases within the internal cell volumes 112, 122, which solution phases are kept thin to minimize concentration dilution. A first electrochemical cell 110 includes the first housing 111 defining the first internal cell volume 112, a first working electrode (WE1) 114 including the sensor 200 therein, a first reference electrode (RE1) 116 therein, and optionally a first counter electrode (CE1) 118 therein. Likewise, a second electrochemical cell 120 includes the second housing 121 defining the second internal cell volume 122, a second working electrode (WE2) 124 including the sensor 300 therein, a second reference electrode (RE2) 126 therein, and optionally a second counter electrode (CE2) 128 therein. A multichannel potentiostat 140 is connected to the working electrodes 114, 124, the reference electrodes 116, 126, and the counter electrodes 118, 128. For a given electrochemical cell 110, 120, potential of the working electrode 114 or 124 is controlled with respect to a fixed potential reference electrode 116 or 126, respectively; current then flows and is measured between the working electrode 114 or 124 and the counter electrode 118 or 128, respectively.

Figure 2A:
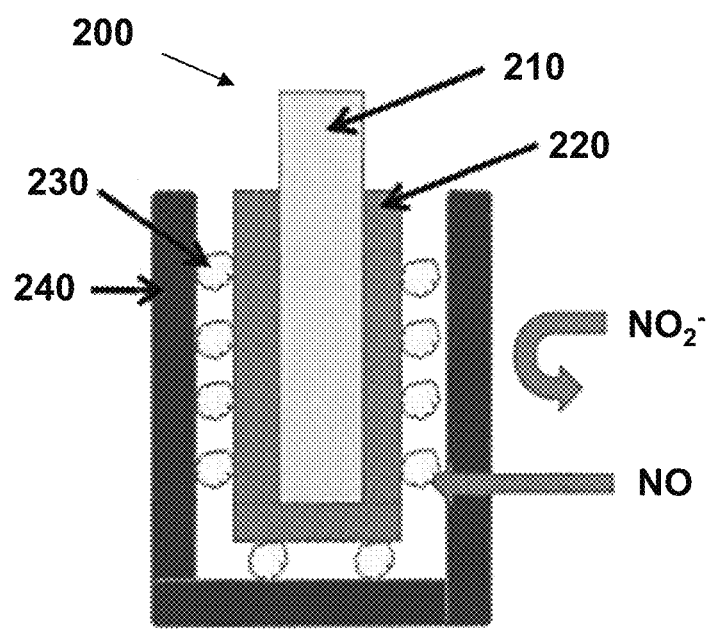
FIG. 2 (A) illustrates a nitric oxide sensor electrode according to the disclosure.

In an embodiment, the nitric oxide sensor 200 utilizes nanoparticles of platinum electrodeposited on boron-doped diamond followed by overcoating the metal particles and diamond with NAFION (FIG. 2 (A)). The platinum lowers the potential for nitric oxide oxidation compared to bare diamond, and the NAFION rejects access of interfering anions.

Figure 2B:
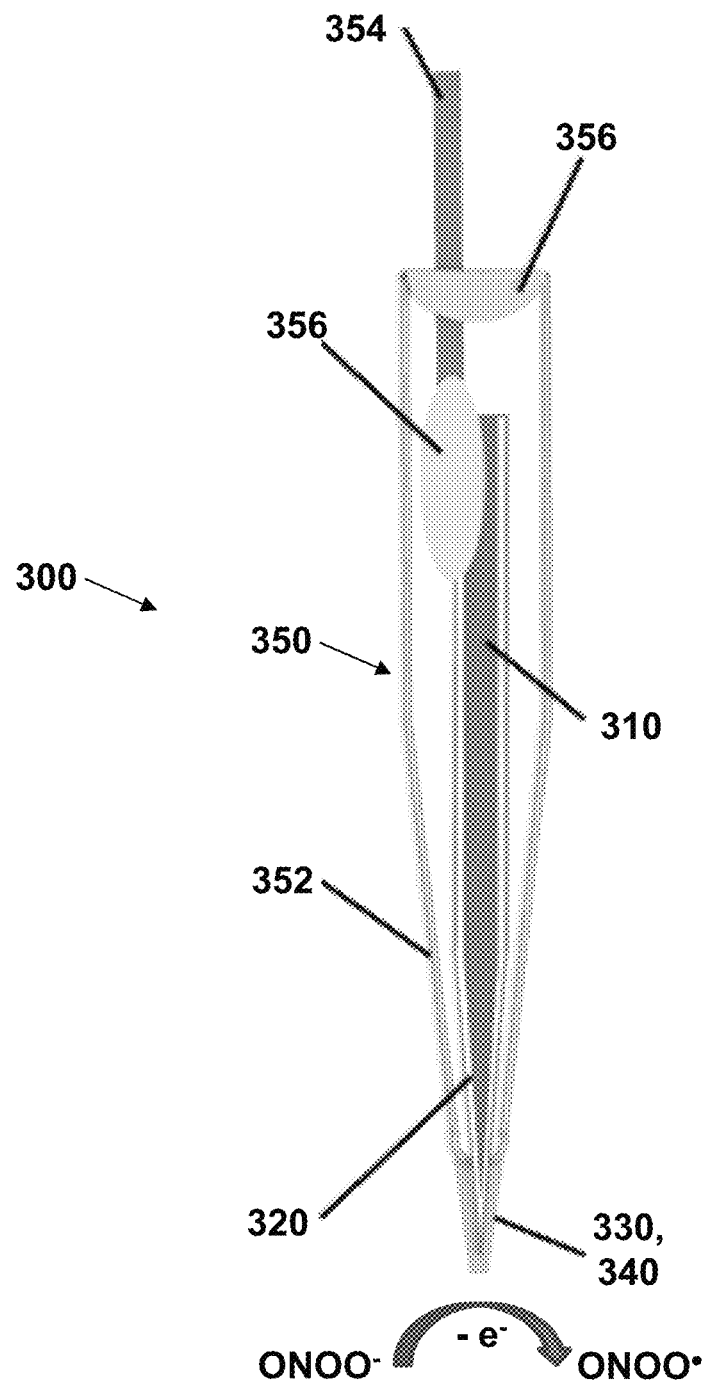

In an embodiment, the peroxynitrite sensor 300 utilizes a diamond microelectrode modified with a layered composite film of poly(3,4-ethylenedioxythiophene) and hemin (iron protoporphyrin IX) with a polyethyleneimine layer coated on the outside to increase selectivity and stability (FIG. 2(B)).

The breath analyzer 100 is designed to provide detection of low ppb levels of nitric oxide (NO) and peroxynitrite (PON) in the exhaled breath of humans or animals. The sensor technology used in the analyzer permits on-site and point-of-care detection of these volatile NO and PON biomarkers that are diagnostics of oxidative stress and inflammation, infection, cancer and other respiratory diseases. The analyzer can assist in the diagnosis and/or treatment of respiratory diseases such as asthma, COPD, cystic fibrosis and lung cancer, where monitoring biomarkers such as NO and PON could have beneficial consequences for therapeutic intervention. The analyzer can be used to detect, analyze, and/or correlate these biomarkers with acute complications associated with lung transplantation (e.g., acute rejection, lymphocytic bronchiolitis, and/or acute infection) and with the development of lung cancer. Using small, portable analyzers according to the disclosure, clinicians could detect and possibly use the NO and/or PON biomarkers as early stage predictors of acute complications.

Breath is primarily a mixture of nitrogen, oxygen, carbon dioxide, water and numerous volatile compounds, including volatile organic compounds. The volatile compounds can vary qualitatively and quantitatively depending on an individual's health status. Of the endogenous volatile compounds, NO is a key biomarker. For example in patients with lung cancer, NO levels are elevated as compared to healthy controls. The same holds true for asthma. In general, NO is recognized as an inflammatory biomarker. It is unclear whether PON levels are elevated in other respiratory diseases such as COPD. The ability to measure PON in the exhaled breath mist of patients, however, would provide unequivocal evidence for oxidative stress and inflammation. Elevations of these two biomarkers in cancer would likely be due to tumor-related non-specific inflammatory mechanisms.

The breath analyzer 100 includes two electrochemical sensors 200, 300. The first electrochemical sensor 200 is a sensing electrode for detection of nitric oxide (NO), and the second electrochemical sensor 300 is a sensing electrode for detection of peroxynitrite (PON). Currently, breath analyzers available for clinical use only measure NO. Many respiratory diseases have associated inflammation. In inflammation, NO levels are reduced and PON levels are elevated. Having a device that can measure the levels of both biomarkers would be a significant advance in respiratory medicine. In the illustrated breath analyzer 100, gas flow will be applied to the outside of gas permeable membranes that separate thin solution layers housing the two sensors 200, 300. The gas flow can be exhaled breath from a human patient or animal, or the gas flow can be an artificial or synthetic source of gas flow (e.g., analogous to exhaled breath, such as containing NO and/or PON gases at appropriate biological levels for the purpose of analyzer testing and/or calibration). In the case of the PON sensor 300, a silicone or polydimethyl siloxane (PDMS) gas permeable membrane 123 can be used. In the case of the NO sensor 200, a sulfonated tetrafluoroethylene copolymer (e.g., NAFION) gas permeable membrane 113 can be used. The external gas flow will cause an equilibrium concentration of the gas or analyte to be established in a thin solution phase within the internal cell volumes 112, 122 via diffusion across the membranes 113, 123. This thin solution phase (e.g., electrolyte solution) is kept thin so as to minimize concentration dilution and to maximize the sensor response time. The multichannel potentiostat 140 connected to the sensor 200, 300 working electrodes 114, 124, reference electrodes 116, 126, and counter electrodes 118, 128 can be used to amperometrically measure independent sensor 200, 300 responses for NO and PON oxidation in each cell as a function of the gas flow rate, gas composition, and the temperature. In another embodiment (not shown), solid-state electrochemical sensing cells can be incorporated into the analyzer 100.

The electrochemical NO sensor 200 is simple in design and uses a diamond microelectrode (FIG. 2 (A)). As illustrated, the sensing electrode 200 for detection of NO includes an electrically conducting substrate 210, an electrically conducting boron-doped diamond (BDD) layer 220 over the electrically conducting substrate 220, metallic nanoparticles 230 for oxidation of nitric oxide NO deposited on the BDD layer 220, and an anionic polyelectrolyte layer 240 over the metallic nanoparticles 230 and the BDD layer 220. The illustrated embodiment includes a platinum wire as the electrically conducting substrate 210, upon which the BDD layer 220 is coated/deposited. The illustrated embodiment further includes nanoparticles 230 of platinum electrodeposited on the BDD diamond layer 220, followed by overcoating of the metal nanoparticles 230 and the BDD diamond layer 220 with a layer of sulfonated tetrafluoroethylene copolymer (e.g., NAFION) as the anionic polyelectrolyte layer 240. The platinum nanoparticles 230 serve to lower the potential for NO oxidation as compared to bare diamond, and the NAFION anionic polyelectrolyte layer 240 functions to reject access of interfering anions, a primary one being nitrite ($NO_2^-$). This is illustrated in FIG. 2 (A) with $NO_2^-$ being rejected by the anionic polyelectrolyte layer 240 and NO being able to pass through the anionic polyelectrolyte layer 240. Diamond microelectrodes are used due to the excellent response sensitivity, reproducibility and stability they offer. The use of the NAFION anionic polyelectrolyte layer 240 as an overlayer effectively rejects anions up to the millimolar (mM) level, and thus there is little or no interfering contribution to the measured current from anionic interferents such as nitrite ($NO_2^-$) or PON (i.e., $ONOO^-$). In a refinement, a thinner and more uniform coating of the anionic polyelectrolyte layer 240 can be applied using a method such as electrocoating, which in turn can decrease sensor response time.

Figure 3:
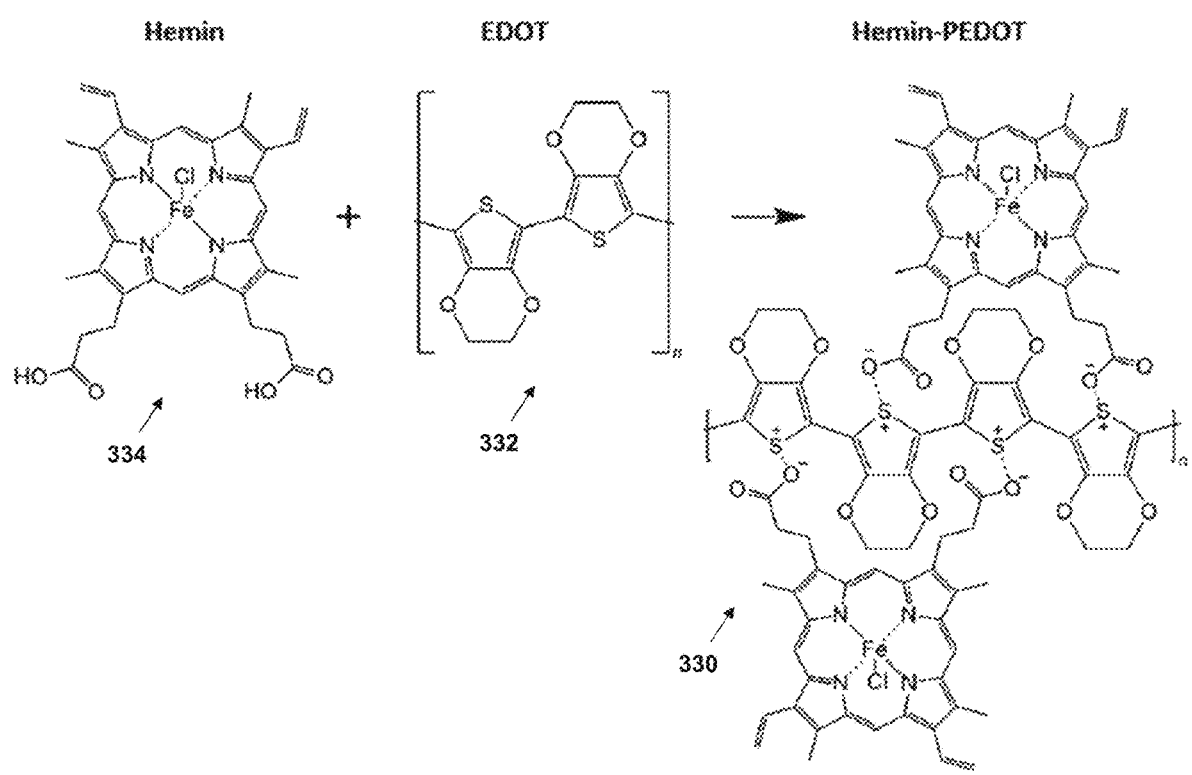
FIG. 3 illustrates a hemin-polyethylenedioxythiophene (PEDOT) film as formed by electropolymerization of ethylenedioxythiophene (EDOT) with hemin.

The electrochemical PON sensor 300 uses a porphyrin-modified electrode for selective and sensitive detection of PON (FIG. 2 (B)). As illustrated, the sensing electrode 300 for detection of PON includes an electrically conducting substrate 310, an electrically conducting boron-doped diamond (BDD) layer 320 over the substrate 310, an electrically conductive polymeric layer 330 over the BDD layer 320, and (optionally) a cationic polyelectrolyte layer 340 over the polymeric layer 330. The electrically conductive polymeric layer 330 includes an electrically conductive polymer 332 and a porphyrin 334 including a complexed metal ion, such as where the porphyrin 334 is incorporated into the conductive polymer 332 network or backbone (e.g., via ionic interactions or bonds therebetween). The illustrated embodiment includes a platinum wire as the electrically conducting substrate 310, upon which the BDD layer 320 is coated/deposited. The illustrated embodiment further includes a layered composite film of poly(3,4-ethylenedioxythiophene) (PEDOT) and hemin (iron protoporphyrin IX) as the polymeric layer 330, the conductive polymer 332, and the porphyrin 334, respectively (FIG. 3). Hemin is an iron protoporphyrin that has peroxide-like activity with the $Fe^{III}/Fe^{IV}$ redox center being the electrocatalytic site. In a refinement, the sensing electrode 300 further includes the cationic polyelectrolyte layer 340, for example a polyethyleneimine (PEI), on the outside/external surface of the sensor 300 to increase selectivity and stability, for example with representative values of 10±0.5 nM PON as a detection limit at signal/noise (S/N) ratio of 3, 4.5±0.5 nA/nM POH as a sensitivity, and 3.5±1 s as a response time.

EXAMPLES

The examples illustrate the disclosed apparatus and methods, but are not intended to limit the scope of any claims thereto. In particular, the examples include illustrative embodiments of the disclosed sensing electrode for detection of peroxynitrite (PON) and related methods for detection thereof.

Peroxynitrite (PON) is a potent nitroxidation agent and highly reactive metabolite, clinically correlated with a rich pathophysiology, and its sensitive and selective detection is challenging due to its high reactivity and short sub-second lifetime. This example illustrates a boron-doped diamond (BDD) microelectrode according to the disclosure with an electropolymerized film of hemin and polyethylenedioxythiophene (PEDOT) that can be used to selectively quantify PON. The sensor's electrochemical response to PON was measured by voltammetry and time-based amperometry. The measured detection limit was 10±0.5 nM (S/N=3), the sensitivity was 4.5±0.5 nA/nM, the response time was 3.5±1 s, and the response variability was 5% or less (RSD). The sensors were stable, maintaining at least 93% of the initial response to 50 nM PON after a 20-day storage in 0.1 M PB (pH 7.4) at 4° C.

Materials:

Iron protoporphyrin IX (hemin), ethylenedioxythiophene, tetrabutylammonium tetrafluoroborate and dichloromethane were purchased from Sigma Aldrich (St Louis, Mo.). Synthetic PON was formed using a stock solution mixing 3-morpholinosydnonimine (SIN-1; available from Cayman Chemical, Ann Arbor, Mich.) with 0.1 M phosphate buffered saline solution (PBS) of pH 7.4 at room temperature, which solution then equilibrates with the air to liberate superoxide anion and nitric oxide spontaneously in solution. Ultra-pure water used for the solution preparations was from a Barnstead ultrapure water system Model D3750 with a resistivity of ≥18 M Ω cm. All other chemicals were reagent grade quality and used as received.

Microelectrode:

FIG. 2 (B) illustrates the BDD microelectrode formed in the example. A boron-doped diamond thin film was deposited on a sharpened 76 µm diameter platinum wire (both ends) using microwave-assisted chemical vapor deposition (1.5 kW, 2.54 GHz reactor). The platinum wire was prepared for growth by (i) ultrasonic cleaning in acetone for 20 min, (ii) ultrasonic seeding from a mixture of detonation diamond (3-6 nm with 30 nm aggregates as per the supplier) and DMSO (0.5 w/v %) for 30 min, (iii) rinsed 3× with ultrapure water, (iv) air dried, and (v) placed in the deposition reactor for pump down to a base pressure of 15 mtorr. BDD deposition was performed using (i) a 1% $CH_4/H_2$ source gas mixture containing 10 ppm diborane ($B_2H_6$) diluted in $H_2$ for doping, (ii) a growth pressure of 35 torr, (iii) a microwave power of 650 W, and (iv) a deposition time of 6-9 h, producing a final film thickness in the 3-5 µm range. The substrates were then cooled in the presence of atomic hydrogen to an estimated temperature of <400° C., by stopping the $CH_4$ and $B_2H_6$ gas flows with the plasma ($H_2$) still ignited, slowly reducing power and pressure over a 30 min period to 150 W and 10 torr to cool the specimens. Post-growth cool-down in atomic hydrogen removes any adventitious $sp^2$ carbon impurity, eliminating any surface reconstruction and for maintaining a stable H surface termination.

The BDD-coated platinum wire was cut in half to form two microelectrodes 300, which were incorporated into an electrode assembly 350. The cut ends of the microelectrodes 300 were then affixed to a copper wire 354 current collector using silver epoxy for conductivity and super glue for mechanical strength as mounting element 356 (FIG. 2 (B)). The BDD microelectrode was then insulated by carefully melting the end of a polypropylene pipette tip (e.g., as a housing 352 for the sensor electrode) in a micro-pipette puller, which causes the polymer to flow over the surface of the BDD-coated platinum wire forming a tight seal and producing a conically-shaped microelectrode with an exposed length of diamond-coated wire of about 500-800 µm.

Hemin-PEDOT Film:

A first hemin-PEDOT film "A" was electropolymerized from a monomer solution of 1.5 mM hemin and 4.5 mM ethylenedioxythiophene (EDOT) in 0.1 M tetrabutyl-ammonium tetrafluoroborate with dichloromethane as the solvent. A second hemin-PEDOT film "B" was prepared with 1.5 mM hemin and 13.5 mM EDOT (3× higher concentration) in 0.1 M tetrabutyl-ammonium tetrafluoroborate with dichloromethane as the solvent. Forty potential sweeps from −1.5 to +1.5 V were applied in deoxygenated solution to deposit the polymer. Deoxygenation was accomplished with a 20 min $N_2$ purge. The solution was blanketed with the gas during the polymer film formation. There was a progressive increase in the redox currents during each voltammetric cycle, indicative of the growth of a hemin-PEDOT film on the immersed microelectrode surface. After each modification step, the microelectrodes were thoroughly rinsed with ultrapure water and then dried under $N_2$. The hemin-PEDOT-modified micro-electrode was covered with a polyethyleneimine (PEI) membrane to increase sensitivity by dip coating three times in a 1.5% aqueous solution of polyethyleneimine (PEI; Sigma-Aldrich), a polymeric amine with high charge density that screens against cation permeation and also prevents fouling.

The BDD microelectrode was immersed in the hemin-EDOT monomer solution in the presence of the organic solvent with supporting electrolyte as indicated above, being cycled 20 times between −1.5 and +1.5 V at 50 mV $s^{-1}$ vs. Ag/AgCl under a $N_2$ gas blanket. The hemin-PEDOT film is formed by electropolymerization with the hemin molecules incorporated into the PEDOT network as shown in FIG. 3. The oxidized conductive polymer returns to a neutral (undoped) semiconductive form upon reduction. The polymer layer increases in thickness with cycle number. The electropolymerization involves an electrogenerated cation radical on the anodic sweep as the reactive species, and polymer formation then proceeds through a series of radical coupling reactions and electrochemical reoxidations. Radical formation and chain growth cause the anodic charge at potentials positive of 0.1 V, and the corresponding cathodic charge to increase with cycle number.

Electrochemistry:

Cyclic voltammetry and continuous amperometry were performed in a 10 mL single-compartment glass cell housed in an electrically grounded Faraday cage. The sensor system included three electrodes: the Hemin-PEDOT-BDD working electrode, an Ag/AgCl (3 M KCl) reference electrode, and a platinum wire counter electrode. The electrodes were connected to CH Instruments 832A (Austin, Tex.) electrochemical workstation. Measurements were performed at 23±1° C. unless otherwise specified.

Figure 4:
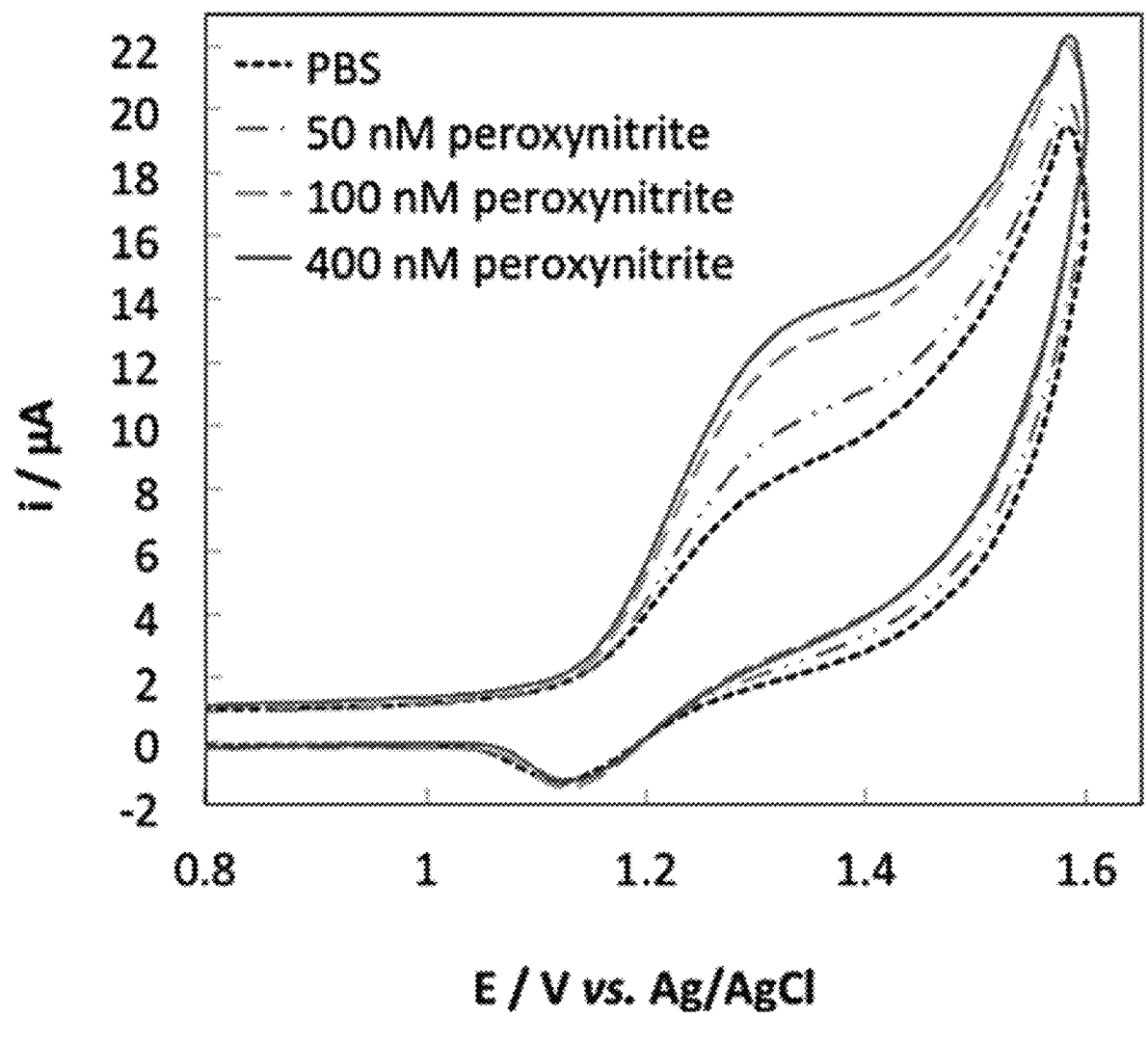
FIG. 4 illustrates cyclic voltammetric i-E curves recorded for different concentrations of PON in 0.1 M PB (pH 7.4) from 50 to 400 nM at a hemin-PEDOT BDD microelectrode (scan rate=100 mV/s). The PON concentration was estimated from the known concentration of SIN-1 (which is a PON generator) and assuming a 1/100 ratio of PON to SIN-1 under steady-state conditions.

Voltammetry:

Cyclic voltammetry was used to assess the redox behavior of the hemin-PEDOT-BDD microelectrode. FIG. 4 shows cyclic voltammograms recorded with different concentrations of PON from 50 to 400 nM. An oxidation peak at +1.35 V vs. Ag/AgCl is seen that increases proportionally with the concentration. PON oxidation occurs concomitantly with the oxidation of $Fe^{3+}$ to $Fe^{4+}$ in the hemin, and the peak on the reverse sweep at +1.15 V is due to the reduction of $Fe^{4+}$ back to $Fe^{3+}$. Previous studies examined the ratio $I/I_0$, which is the peak current of the voltammetric wave of the modified electrode in the presence of PON (I) relative to the current measured in absence of the analyte at same potential ($I_0$), and the ratio depends on the scan rate, gradually decreasing as the scan rate increased for all concentrations studied. This behavior is typical of an electrocatalytic process where the oxidation of PON is mediated by the hemin polymeric film. The catalytic process as described above was not observed with films of protoporphyrin-only (i.e., lacking the iron or other metallic ion) suggesting the critical role played by the bound iron atom in the hemin-based films. The iron metal center is responsible for the oxidative catalytic turnover of PON, mediating the inner electron transfer from the PON substrate to the oxidizing porphyrin ring, which acts as an "antenna" for oxidizing equivalents from the electrode.

Amperometry:

PON was also detected using continuous amperometry with the hemin-PEDOT-BDD microelectrode poised at +1.35 V vs. Ag/AgCl. The current was recorded in response to varying aliquots (5, 10, 50, 100 μL) of the SIN-1/PON stock solution added to the electrochemical cell containing a magnetically-stirred phosphate buffer solution at pH 7.4. The limiting current scales proportionally with an increase in the PON concentration. The lowest detectable concentration was 10±0.5 nM (S/N=3) with a 3.5±1 s response time (i.e., the time required to reach 90% of the maximum current). The sensor response variability was 5% RSD, and the sensor sensitivity was 4.5±0.5 nA/nM.

Electrode Sensitivity:

The sensitivity to PON of differently modified BDD microelectrodes was evaluated for unmodified, hemin-only, PEDOT-only, hemin-PEDOT type A, and hemin-PEDOT type B BDD microelectrodes. The type B electrode consisted of a PEDOT layer formed from 3× higher concentration of the EDOT monomer in solution as compared to type A electrode. The sensitivities for the different microelectrodes were as follows: 0.05-0.06 nA/nM for the unmodified, 0.8-0.9 nA/nM for hemin-only; 0.7-0.8 nA/nM PEDOT type A-only; 1.9-2.1 nA/nM for hemin-PEDOT type A; and 5.0-5.5 nA/nM for hemin-PEDOT type B BDD microelectrodes. The increased loading of PEDOT leads to increased sensor sensitivity, likely due to a greater number of hemin molecules in the thicker PEDOT layer available for coordination with PON. Specifically, a 3-fold increase in the EDOT monomer content used for the film formation (i.e., greater PEDOT loading) produced a 2.8 fold increase in the sensitivity to PON (i.e., hemin-PEDOT film B compared with hemin-PEDOT film A). Polythiophene is attractive for modified electrodes because of the rich functionalization afforded by its monomer ring, and it also offers good electrical conductivity and high stability. The EDOT has been especially preferred for several reasons. The two oxygen atoms coupled to the thiophene rings permit monomer to be oxidized at lower potentials. PEDOT offers high electrical conductivity and a narrow bandgap, being easily oxidized over a wide anodic potential window. PEDOT is a highly conductive polymer that supports electron transfer from the catalytic hemin sites in the film to the electrode. Thus, the hemin and PEDOT combine to provide a catalytic and electrically conducting layer for PON oxidation.

Sensor Selectivity, Reproducibility, and Stability:

The hemin-PEDOT film was covered with a polyethyleneimine (PEI) layer to improve response selectivity. The selectivity of the hemin-PEDOT-PEI BDD micro-electrode for PON was evaluated in the presence of several potential interfering electroactive species, namely norepinephrine, serotonin and uric acid at a 140-fold higher concentration of the interfering analyte as compared to PON. All of three compounds would undergo diffusion limited oxidation at BDD in PBS solution at the PON detection potential of 1.35 V vs. Ag/AgCl. The tests indicated that the response of each interferent was only about 6-7% when compared with the PON response, which is considered to be 100%. The PEI layer aids in the rejection of the cationic norepinephrine and serotonin (pH 7.4). These are interferents that would be encountered in in vitro studies in the gut wall. Surprisingly, there is also good rejection of the urate ion. The reproducibility of the hemin-PEDOT-PEI BDD microelectrode was assessed using 50 nM PON. Five microelectrode sensors were prepared and the continuous amperometric response to PON was measured. A relative standard deviation (RSD) of 5.8% was determined, indicating good sensor reproducibility. To assess the longer-term response stability, five microelectrode sensors were stored in 0.1 M PB (pH 7.4) at 4° C. in glass vials with the tops wrapped using parafilm. After 20 days, the microelectrode sensors were removed and used in continuous amperometry to measure 50 nM PON mixed with 0.1 M PB (pH 7.4). All five sensors retained greater than 93% of their initial responses to 50 nM PON.

Figure 5:
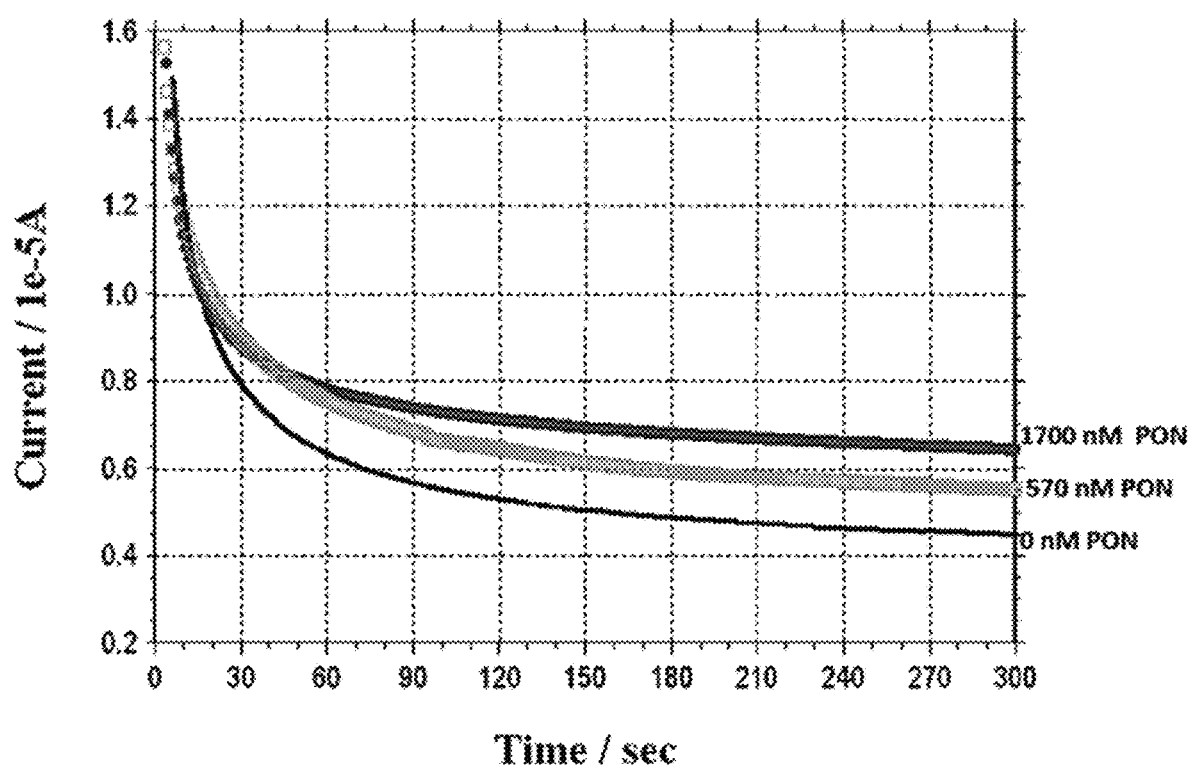
FIG. 5 illustrates amperometric i-E curves recorded for different concentrations of gas-phase PON in water vapor (0, 570, and 1700 nM) at a hemin-PEDOT BDD microelectrode.

The foregoing example tested the ability of various hemin-PEDOT BDD microelectrodes to detect PON in an aqueous liquid solution. In a sample of human or animal breath to be tested for PON, the PON would be present in the gas phase along with other typical breath components (e.g., oxygen, nitrogen, water, carbon dioxide). The hemin-PEDOT BDD microelectrodes were further tested for their ability to detect gas-phase PON by sparging nitrogen gas through water and into a vessel containing air (nitrogen and oxygen) and freshly generated PON, thereby creating a gas-phase mixture of PON in water vapor and air, which was then delivered to an electrochemical cell including a hemin-PEDOT BDD microelectrode for PON detection. FIG. 5 illustrates amperometric i-E curves recorded for different concentrations of the gas-phase PON in water vapor (0, 570, and 1700 nM PON) at the hemin-PEDOT BDD microelectrode. As shown in FIG. 5, increasing current response with increasing concentration of PON in the misting solution demonstrates the ability of the PON electrode sensor according the disclosure to detect and quantify P Peteu et al., "Electrochemical detection of peroxynitrite using hemin-PEDOT functionalize boron-doped diamond," Analyst, vol. 141, pp. 1796-1806 (available online Feb. 2, 2016) includes further description of the PON electrode and sensor according to the disclosure and is incorporated herein by reference in its entirety.

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the apparatus, compounds, compositions, methods, and processes are described as including components, steps, or materials, it is contemplated that the compositions, processes, or apparatus can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

PARTS LIST 100 electrochemical sensor for detecting nitric oxide (NO) and peroxynitrite (PON)
110 first electrochemical cell
111 first housing
112 first internal cell volume
113 first gas-permeable membrane
114 first working electrode (WE1)
116 first reference electrode (RE1)
118 first counter electrode (CE1)
120 second electrochemical cell
121 second housing
122 second internal cell volume
123 second gas-permeable membrane
124 second working electrode (WE2)
126 second reference electrode (RE2)
128 second counter electrode (CE2)
130 sample gas flow inlet
132 fluid communication conduit
134, 134' particulate filter
136 inlet gas mass flow controller
140 potentiostat
200 sensing electrode for detection of nitric oxide (NO)
210 electrically conducting substrate
220 electrically conducting boron-doped diamond (BDD) layer
230 metallic nanoparticles for oxidation of nitric oxide (NO)
240 anionic polyelectrolyte layer
300 sensing electrode for detection of peroxynitrite (PON)
310 electrically conducting substrate
320 electrically conducting boron-doped diamond (BDD) layer
330 electrically conductive polymeric layer
332 electrically conductive polymer
334 porphyrin with complexed metal ion
340 cationic polyelectrolyte layer
350 electrode assembly structure
352 housing/mounting unit
354 external electrical connection/wire
356 mounting elements (resin or adhesive plugs or connectors)

What is claimed is:

1. A method for detecting nitric oxide (NO) and peroxynitrite (PON), the method comprising:
   (a) providing an electrochemical sensor comprising:
      (A) a first electrochemical cell comprising (i) a first housing defining a first internal cell volume, (ii) a first working electrode (WE1) in the first internal cell volume for detection of nitric oxide (NO), (iii) a first reference electrode (RE1) in the first internal cell volume, (iv) optionally a first counter electrode (CE1) in the first internal cell volume, and (v) a first liquid electrolyte medium in the first internal cell volume with the WE1, RE1, and CE1 electrodes immersed therein,
      wherein the first working electrode (WE1) comprises: a first electrically conducting substrate; a first electrically conducting boron-doped diamond (BDD) layer over the first electrically conducting substrate; first metallic nanoparticles for oxidation of nitric oxide (NO), the first metallic nanoparticles being deposited on the first electrically conducting BDD layer; and a first anionic polyelectrolyte layer over the first metallic nanoparticles and the first electrically conducting BDD layer; and
      (B) a second electrochemical cell comprising (i) a second housing defining a second internal cell volume, (ii) a second working electrode (WE2) in the second internal cell volume for detection of peroxynitrite (PON), (iii) a second reference electrode (RE2) in the second internal cell volume, (iv) optionally a second counter electrode (CE2) in the second internal cell volume, and (v) a second liquid electrolyte medium in the second internal cell volume with the WE2, RE2, and CE2 electrodes immersed therein,
      wherein the second working electrode (WE2) comprises: a second electrically conducting substrate; a second electrically conducting boron-doped diamond (BDD) layer over the second electrically conducting substrate; a second electrically conductive polymeric layer over the second electrically conducting BDD layer, the second electrically conductive polymeric layer comprising (i) an electrically conductive polymer and (ii) a porphyrin comprising a complexed metal ion; and
      optionally a second cationic polyelectrolyte layer over the second electrically conductive polymeric layer;
   (b) delivering a sample containing or suspected of containing at least one of nitric oxide (NO) and peroxynitrite (PON) to the first liquid electrolyte medium and the second liquid electrolyte medium; and
   (c) electrochemically detecting, using the electrochemical sensor, the nitric oxide present in the first electrochemical cell, and electrochemically detecting, using the electrochemical sensor, the peroxynitrite present in the second electrochemical cell.

2. The method of claim 1, wherein the first liquid electrolyte medium and the second liquid electrolyte medium comprise a phosphate-buffered saline solution.

3. The method of claim 1, wherein the sample contains at least one of nitric oxide and peroxynitrite as a target analyte.

4. The method of claim 1, wherein electrochemical detection comprises:
   applying a first voltage differential to the first electrochemical cell WE1, RE1, and CE1 electrodes measuring a corresponding electrical current though the first electrochemical cell; and
   applying a second voltage differential to the second electrochemical cell WE2, RE2, and CE2 electrodes measuring a corresponding electrical current though the second electrochemical cell.

5. The method of claim 1, further comprising:
   (d) quantitatively determining the amount of the nitric oxide and the peroxynitrite in the sample.

6. The method of claim 1, wherein the sample is an exhaled breath sample from a human or animal.

7. The method of claim 6, wherein:
   the first electrochemical cell further comprises a first gas-permeable membrane at a boundary of the first internal cell volume;
   the second electrochemical cell further comprises a second gas-permeable membrane at a boundary of the second internal cell volume;
   the electrochemical sensor further comprises a sample gas flow inlet coupled to and in fluid communication with the first gas-permeable membrane and the second gas-permeable membrane; and
   delivering the sample comprises exhaling the breath sample into the gas flow inlet such that any nitric oxide present in the breath sample passes through the first gas-permeable membrane and into the first liquid electrolyte medium of the first electrochemical cell, and any peroxynitrite present in the breath sample passes through the second gas-permeable membrane and into the second liquid electrolyte medium of the second electrochemical cell.

8. The method of claim 1, wherein:
   the first electrochemical cell further comprises a first gas-permeable membrane at a boundary of the first internal cell volume; and
   the second electrochemical cell further comprises a second gas-permeable membrane at a boundary of the second internal cell volume.

9. The method of claim 8, wherein the electrochemical sensor further comprises a sample gas flow inlet coupled to and in fluid communication with the first gas-permeable membrane and the second gas-permeable membrane.

10. The method of claim 8, wherein:
    the first gas-permeable membrane comprises an anionic polyelectrolyte membrane; and
    the second gas-permeable membrane comprises a polysiloxane membrane.

11. The method of claim 1, wherein:
    the first reference electrode (RE1) and the second reference electrode (RE2) are Ag/AgCl electrodes; and
    the first counter electrode (CE1) and the second counter electrode (CE2) are platinum wire electrodes.

* * * * *